United States Patent
Housman et al.

(10) Patent No.: US 6,420,122 B1
(45) Date of Patent: Jul. 16, 2002

(54) METHODS OF SCREENING FOR AGENTS THAT INHIBIT AGGREGATION OF POLYPEPTIDES

(75) Inventors: David E. Housman, Newton; Elizabeth A. Preisinger, Roslindale; Aleksey G. Kazantsev, Boston, all of MA (US)

(73) Assignee: Massachusetts Institute of Technology, Boston, MA (US)

( * ) Notice: Subject to any disclaimer, the term of this patent is extended or adjusted under 35 U.S.C. 154(b) by 0 days.

(21) Appl. No.: 09/405,048

(22) Filed: Sep. 27, 1999

(51) Int. Cl.$^7$ .............................................. G01N 33/53
(52) U.S. Cl. ........................... 435/7.1; 435/4; 436/501; 530/300; 530/350
(58) Field of Search .................. 436/86, 501; 536/23.4; 530/300, 350; 435/7.1, 4

(56) References Cited

U.S. PATENT DOCUMENTS 5,688,651 A 11/1997 Solomon

FOREIGN PATENT DOCUMENTS

WO    WO 97/17443    *   5/1997    .......... C12N/15/12
WO    WO 99/29891       6/1999

OTHER PUBLICATIONS

Rogers, Kenneth S, Protein Fluorescence and inactivation of glutamate dehydrogenase during treatment with silver, 36(3), 153–60, 1969.*
No David et al, Ecdysone–inducible gene expression in mammalian cells and transgenic mice, PNAS, 93(8), 3346–3351, 1996.*
Molecular Probes, Inc., Eugene, Oregon, 1975.*
Harlow Ed and David Land, Anitbodies, A Laboratory Manual, Cold Spring Harbor Press, Chapter 5, p124, 1988.*
Carmichael et al., *J. of Bio. Chem.* 275:10437–10442, 2000.
Kazantsev et al., *Proceedings National Academy of Science* 96:11404–11409, 1999.
Miyashita et al., *Biochem. & Biophysical Research Comm.* 249:96–102, 1998.
Moulder et al., *J. of Neurosci.* 19:705–715, 1999.
Nagai et al., *J. of Bio. Chem.* 275:10437–10442, 2000.
Davies et al., "Formation of Neuronal Intranuclear Inclusions Underlies the Neurological Dysfunction in Mice Transgenic for the HD Mutation", *Cell*, vol. 90, No. 3, pp. 537–548 (1997).
Li et al., "Aggregation of N–terminal huntingtin is dependent on the length of it glutamine repeats", *Human Molecular Genetics*, vol. 7, No. 5, pp. 777–782 (1998).

Mangiarini et al., "Exon 1 of the *HD* Gene with an Expanded CAG Repeat Is Sufficient to Cause a Progressive Neurological Phenotype in Transgenic Mice", *Cell*, vol. 87, No. 3, pp. 493–506 (1996).
Paulson et al., "Intranuclear Inclusions of Expanded Polyglutamine Protein in spinocerebellar Ataxia Type 3", *Neuron*, vol. 19, No. 2, pp. 333–344 (1997).
Perutz et al., "Glutamine repeats as polar zippers: Their possible role in inherited neurodegenerative diseases", *Proc. Natl. Acad. Sci. USA*, vol. 91, No. 12, pp. 5355–5358 (1994).
Reddy et al., "The complex pathology of trinucleotide repeats", *Current Biology Ltd.*, vol. 9, No. 3, pp. 364–372 (1997).
Ross, "Intranuclear Neuronal Inclusions: A Common Pathogenic Mechanism for Glutamine–Repeat Neurodegenerative Diseases?", *Neuron*, vol. 19, pp. 1147–1150 (1997).
Scherzinger et al., "Huntingtin–Encoded Polyglutamine Expansions From Amyloid–like Protein Aggregates In Vitro and In Vivo", *Cell*, vol. 90, No. 3, pp. 549–558 (1997).
Skinner et al., "Ataxin–1 with an expanded glutamine tract alters nuclear matrix–associated structures", *Nature*, vol. 389, pp. 971–974 (1997).
White et al., "Huntingtin is required for neurogenesis and is not impaired by the Huntington's disease CAG expansion", *Nature Genetics*, vol. 17, No. 4, pp. 404–410 (1997).
The Huntington's Disease Collaborative Research Group, "A Novel Gene Containing a Trinucleotide Repeat That Is Expanded and Unstable on Huntington's Disease Chromosomes", vol. 72, No. 6, pp. 971–983 (1993).
Ambrose et al., "Structure and Expression of the Huntington's Disease Gene: Evidence against Simple Inactivation Due to an Expanded CAG Repeat", *Somatic Cell and Molecular Genetics*, vol. 20, No. 1, pp. 27–38 (1994).
Cooper et al., "Truncated N–terminal fragments of huntingtin with expanded glutamine repeats form nuclear and cytoplasmic aggregates in cell culture", *Human Molecular Genetic*, vol. 7, No. 5, pp. 783–790 (1998).
Cummings et al., "Chaperone suppression of aggregation and altered subcellular proteasome localization imply protein misfolding in SCA1", *Nature Genetics*, vol. 19, No. 2, pp. 148–154 (1998).

* cited by examiner

*Primary Examiner*—Jeffrey Stucker
*Assistant Examiner*—Ulrike Winkler
(74) *Attorney, Agent, or Firm*—Fish & Richardson P.C.

(57) ABSTRACT

Methods of identifying compounds that disrupt aggregation of aggregation-disposed polypeptides, such as huntingtin or beta-amyloid protein, are disclosed. Furthermore, an artificial polypeptide that contains an extended polyglutamine region and DNA that encodes the polypeptide are also disclosed.

34 Claims, No Drawings

METHODS OF SCREENING FOR AGENTS THAT INHIBIT AGGREGATION OF POLYPEPTIDES

STATEMENT AS TO FEDERALLY SPONSORED RESEARCH

This invention was made with Government support under grant number PO1-CA42063, awarded by the National Institutes of Health. The government may have certain rights in the invention.

FIELD OF THE INVENTION

The invention relates to methods of identifying compounds that disrupt polypeptide aggregation. The identified compound can be used to treat disorders associated with such aggregation. Huntington's disease and Alzheimer's disease are examples of these disorders.

BACKGROUND OF THE INVENTION

Huntington's disease (HD) is an autosomal dominant, progressive, neurodegenerative disorder associated with selective neuronal cell death, occurring primarily in the cortex and striatum. The disorder is caused by a CAG codon repeat expansion in the first exon of a gene encoding a 350 kD protein, huntingtin, with unknown function (Ambrose et al., Somat Cell Mol. Genet. 20:27–38, 1994). CAG encodes the amino acid glutamine ("Gln" or "Q"), so CAG repeats encode polyglutamine regions within huntingtin. The polyglutamine region of huntingtin from non-HD individuals contains about 8–31 consecutive Gln residues. Huntingtin with over 37 consecutive Gln residues is associated with mild to severe HD, with the more severe cases exhibiting a polyglutamine region of up to about 68 Gln residues.

In addition to HD, at least six other inherited neurodegenerative disorders have been found to be associated with CAG expansions. Increasing the length of CAG repeats in the coding region of unrelated genes, and resulting polyglutamine regions in the encoded proteins, causes a similar pattern of neuron degeneration, indicating a similar, if not identical, mechanism of cell death. HD may be caused by abnormal protein-protein interactions mediated by elongated polyglutamines.

SUMMARY OF THE INVENTION

The invention is based, in part, on the discovery of a method for identifying compounds that disrupt the aggregation of polypeptides. These compounds are potentially useful as therapeutics for the treatment of disease conditions associated with such aggregation.

Accordingly, the invention features a method of identifying a compound which disrupts polypeptide aggregation. The method includes: providing a first polypeptide which is labelled with a detection moiety (e.g., an enzyme or a fluorescent protein) that is inactive in the presence of a denaturant, and a second polypeptide (which can be identical to the first), wherein the first and second polypeptides aggregate upon contact; contacting the first polypeptide, the second polypeptide and a test compound to form a mixture; contacting the mixture with the denaturant; and determining the activity of the detection moiety. A decrease in the activity following contact of the mixture with the denaturant indicates that the test compound has prevented at least some of the polypeptides from aggregating, thereby leaving them susceptible to inactivation by the denaturant. Such an outcome suggests that the test compound is a polypeptide aggregation disrupting compound. In the above method, the first or second polypeptide can be immobilized, or they both can be in solution. Alternatively, they can be within a cell, e.g., a cell transfected with a DNA encoding the first polypeptide and/or the second polypeptide. The first and second polypeptides can be identical or different, so long as they aggregate upon contact. The first and second polypeptides can be polypeptides that contain an extended polyglutamine region, beta-amyloid polypeptides, tau proteins, presenilins, alpha-synucleins and prion proteins. Examples of naturally occurring polypeptides that contain extended polyglutamine regions are huntingtin, atropin-1, ataxin-1, ataxin-2, ataxin-3, ataxin-7, alpha 1A-voltage dependent calcium channel, and androgen receptor. Non-naturally occurring polypeptides that contain an extended polyglutamine region are polypeptides which include at least 32 consecutive glutamine residues. In the above method, the detection moiety is preferably a fluorescent protein or an enzyme such as luciferase, and the extended polyglutamine region is preferably at least 33, 34, 35, 36, 37, 40, 42, 47, 50, 52, 60, 65, 70, 72, 75, 80, 85, 95, 100, 104, 110, 119, 120, 130, 140, 144, 151, 160, 170, 180, 190, 191, 195, 200, 210, 230, 250, 270 or 300 glutamine residues in length.

Alternatively, the method includes: providing a fluorescently labelled first polypeptide, wherein the first polypeptide contains an extended polyglutamine region; providing a second polypeptide containing an extended polyglutamine region; contacting the first polypeptide, the second polypeptide and a test compound to form a mixture; denaturing unaggregated polypeptides in the mixture; and detecting fluorescence, wherein a decrease in fluorescence in the presence of the test compound indicates that the test compound is a polypeptide aggregation disrupting compound. The first and second polypeptides can be naturally or non-naturally occurring polypeptides that have at least 32 consecutive glutamine residues. As above, the first or the second polypeptide can be immobilized or both polypeptides can be in solution. Alternatively, they can be within a cell, e.g., a transfected cell which expresses both polypeptides.

Another method of identifying a compound which disrupts the aggregation of polypeptides containing extended polyglutamine regions includes providing a cell which is genetically modified to express a DNA encoding a heterologous polypeptide containing an extended polyglutamine region; contacting the cell with a test compound; and determining whether the test compound decreases the amount of aggregation of the polypeptide in the cell, wherein a decrease in polypeptide aggregation in the presence of the test compound indicates that the test compound is a polypeptide aggregation disrupting compound. The heterologous polypeptide can be, for example, a fusion protein comprising an antigenic tag or a label. Examples of labels include fluorescent proteins (e.g., a green fluorescent protein (GFP) or a blue fluorescent protein (BFP)) and enzymes. Where the label is a fluorescent protein or other denaturable protein, the step of determining whether the compound is an aggregation disrupting compound includes contacting the cell with a denaturant such as detergent or heat sufficient to effect denaturing of the label portion of unaggregated fusion protein, and detecting fluorescence wherein a decrease in fluorescence following contact of the cell with the denaturant, compared to fluorescence in a similar cell that is treated with the denaturant but not the test compound, indicates that the compound is a polyglutamine polypeptide aggregation disrupting compound. The expression of the DNA can be inducible, e.g., expression can be induced upon exposure of the cell to an inducing agent such as ecdysone or muristerone.

A final method of identifying a compound which disrupts the aggregation of polypeptides includes the steps of providing a cell that is genetically modified to express a DNA encoding a heterologous polypeptide, wherein molecules of the polypeptide spontaneously aggregate within the cell; contacting the cell with a test compound; and determining whether molecules of the polypeptide aggregate in the presence of the test compound, wherein a decrease in aggregation of the polypeptide molecules in the presence of the test compound indicates that the test compound is a polypeptide aggregation disrupting compound. The polypeptide can be a fusion protein comprising a label such as a fluorescent protein (e.g., a GFP or a BFP) or an enzyme. The method can further include contacting the cell with a denaturant such as a detergent or heat, and detecting fluorescence or other activity of the label, wherein a decrease in fluorescence or activity compared to a control not exposed to the test compound indicates that the compound is a polypeptide aggregation disrupting compound.

The invention features a DNA encoding a fusion protein which includes (a) at least 32 contiguous glutamine residues and (b) a label (e.g., a fluorescent protein such as GFP or BFP or an enzyme such as luciferase), wherein the sequence encoding the at least 32 glutamine residues comprises both CAG codons and CAA codons. The CAG and CAA codons can be present as a mixture in the DNA, e.g., containing the sequence CAA CAG CAG CAA CAG CAA (SEQ ID NO:1), e.g., (CAA CAG CAG CAA CAG CAA)n (SEQ ID NO:1), where n can be between 7–300, e.g., n is 5, 6, 7, 8, 9, 10, 11, 12, 13, 14, 15, 16, 17, 18, 19, 20, 21, 22, 23, 24, 25, 26, 27, 28, 29, or 30. The CAG and CAA codons need not be present in equal numbers. For example, CAA could be every third or fourth codon in the polyglutamine-encoding DNA. The CAG and CAA codons can be present in a repeating pattern, or can be a random mixture.

Other possible labels include other florescent proteins, enzymes, and any other protein which can be used to distinguish between aggregated and non-aggregated polyglutamine-containing proteins. The invention further features a cultured, genetically modified cell which expresses the above described DNA, and a method of producing a fusion protein, comprising culturing the genetically modified cell under conditions appropriate for expressing the DNA encoding the fusion protein.

Also within the invention is a fusion polypeptide comprising (a) at least 32 contiguous glutamine residues and (b) a fluorescent protein such as a GFP or BFP. In preferred embodiments, the polyglutamine region contains at least 33 glutamine residues, and more preferably at least 34, 35, 36, 37, 40, 42, 47, 50, 52, 60, 65, 70, 72, 75, 80, 85, 95, 100, 104, 110, 119, 120, 130, 140, 144, 151, 160, 170, 180, 190, 191, 195, 200, 210, 230, 250, 270 or 300.

The invention also features an expression plasmid which (1) includes a DNA sequence which encodes a fusion protein of (a) at least 32 contiguous glutamine residues and (b) a label, wherein the sequence that encodes the at least 32 glutamine residues includes both CAG codons and CAA codons, and (2) is operably linked to an expression control sequence.

An expression control sequence "operably linked" to a coding sequence is placed so that it controls expression of the latter.

An "isolated DNA" is a DNA which has a non-naturally occurring sequence, or which has the sequence of part or all of a naturally occurring gene but is free of the genes that flank the naturally occurring gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Specifically excluded from this definition are DNA molecules as they occur in a random library, such as a cDNA or genomic DNA library.

A "polypeptide" is any peptide-linked chain of amino acids, regardless of length or post-translational modification.

An "heterologous polypeptide" is defined in reference to a given cell: i.e., it is a polypeptide that is not normally expressed in more than a trace amount within the given cell. A polypeptide with a non-naturally occurring sequence (e.g., the fusion proteins of the invention) is heterologous to all cell types. Even a polypeptide with a naturally occurring sequence (e.g., human huntingtin) would be considered an heterologous polypeptide if it were expressed in a non-human cell, or in a human cell in which it is not normally expressed in more than a trace amount.

An "aggregation-disposed polypeptide" refers to a polypeptide which aggregates with a second polypeptide when contacted with the latter. The second polypeptide can have the same or a different sequence.

An "inducing agent" is an agent that triggers or increases expression of a coding sequence.

The term "label", as used herein, refers to a detection moiety whose detection properties are altered either (i) directly as a consequence of polypeptide aggregation or (ii) upon exposure to an agent following polypeptide aggregation.

The term "aggregation" refers to a process whereby polypeptides stably associate with each other to form a multimeric, insoluble complex, which does not disassociate under physiological conditions.

An "extended polyglutamine region" refers to a region of 32 or more (e.g., at least 33, 34, 35, 36, 37, 40, 42, 47, 50, 52, 60, 65, 70, 72, 75, 80, 85, 95, 100, 104, 110, 119, 120, 130, 140, 144, 151, 160, 170, 180, 190, 191, 195, 200, 210, 230, 250, 270 or 300) consecutive glutamine residues. Polypeptides that contain such regions aggregate upon contact though not necessarily immediately.

A "conservative amino acid substitution" is one in which the amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Percent sequence identity" of two amino acid sequences or of two nucleic acids is determined using the algorithm of Karlin and Altschul (Proc. Natl. Acad. Sci. USA 87: 2264–2268, 1990) modified as in Karlin and Altschul (Proc. Natl. Acad. Sci. USA 90: 5873–5877, 1993). Such an algorithm is incorporated into the NBLAST and XBLAST programs of Altschul et al. (J. Mol. Biol. 215: 403–410, 1990). BLAST nucleotide searches are performed with the NBLAST program, score=100, wordlength=12 to obtain nucleotide sequences homologous to nucleic acid molecules of the invention. BLAST protein searches are performed with the XBLAST program, score=50, wordlength=3 to obtain amino acid sequences homologous to an aggregation-disposed polypeptide. To obtain gapped alignments for comparison purposes, Gapped BLAST is utilized as described in Altschul et al. Nucleic Acids Res. 25:3389–3402, 1997). When utilizing BLAST and Gapped BLAST programs, the default parameters of the respective programs (e.g., XBLAST and NBLAST) are used.

Unless otherwise defined, all technical and scientific terms used herein have the same meaning as commonly understood by one of ordinary skill in the art to which this invention belongs. In case of conflict, the present application, including definitions, will control. All publications, patent applications, patents, and other references mentioned herein are incorporated by reference. The materials, methods, and examples are illustrative only and not intended to be limiting. Other features and advantages of the invention will be apparent from the detailed description, and from the claims.

DETAILED DESCRIPTION OF THE INVENTION

The invention is based, in part, on the discovery of a method which can be used to identify compounds which inhibit the aggregation of polypeptides. The aggregation of certain naturally occurring polypeptides is often associated with pathological disorders such as Alzheimer's disease, Parkinson's disease and Huntington's disease. A compound which inhibits aggregation of naturally occurring aggregation-disposed polypeptides can be used to treat a subject at risk for such a disorder.

Polypeptides

The invention includes screening methods which are used to identify compounds which can disrupt the aggregation of aggregation-disposed polypeptides. An aggregation-disposed polypeptide can be a naturally occurring polypeptide or a non-naturally occurring polypeptide.

The aggregation of naturally occurring polypeptides is often associated with pathological disorders. Examples of naturally occurring polypeptides which aggregate include polypeptides which contain extended polyglutamine regions, herein defined to mean at least 32 contiguous glutamine residues. Such polypeptides and their associated disorders are as follows: huntingtin, which is associated with Huntington's disease; atrophin-1, which is associated with dentatorubralpallidoluysian atrophy; ataxin-1, which is associated with spinocerebellar ataxia type 1; ataxin-2, which is associated with spinocerebellar ataxia type-2; ataxin-3, which is associated with spinocerebellar ataxia type-3; alpha 1a-voltage dependent calcium channel, which is associated with spinocerebellar ataxia type-6; ataxin-7, which is associated with spinocerebellar ataxia type-7; and androgen receptor, which is associated with spinobulber muscular atrophy. Other naturally occurring polypeptides known for their ability to aggregate include the synuclein proteins, namely alpha, beta and gamma synucleins. Synucleins have been implicated in Alzheimer's disease, Parkinson's disease and breast cancer. Proteins such as amyloid light chains and amyloid-associated proteins, which are associated with amyloidosis, can also be used in the methods of the invention. Other aggregation-disposed polypeptides include: mutant transthyretin, which is associated with familial amyloid polyneuropathies; beta2 microglobulin, aggregation of which causes complications during chronic renal dialysis; beta amyloid protein, which is associated with Alzheimer's disease; immunoglobulin light chain, which is associated with multiple myelomas and various other B-cell proliferations; and prion proteins, which cause spongiform encephalopathies like Creutzfeldt-Jakob disease and kuru in humans.

Non-naturally occurring, aggregation-disposed polypeptides include variants of naturally occurring polypeptides, as well as polypeptides which do not occur in nature but have the ability to aggregate, particularly where such polypeptides can be used to model naturally-occurring, disease-associated proteins such as huntingtin and beta amyloid protein. These include polypeptides which are engineered to include regions, such as an extended polyglutamine region, which are known to promote polypeptide aggregation.

Naturally occurring polypeptides of the invention can be obtained by isolating and purifying the protein from a natural source. Alternatively, both naturally and non-naturally occurring aggregation-disposed polypeptides can be produced recombinantly or chemically synthesized by conventional methods. An aggregation-disposed polypeptide, full-length or truncated, can also be part of a fusion protein, e.g., the protein can be fused to an antigenic tag such as c-myc or proteinaceous label such as a green fluorescent protein (GFP).

Techniques for generating polypeptides are well known in the art. A typical method involves transfecting host cells (e.g., bacterial cells, insect cells, mammalian cells, or plant cells) with an expression vector carrying a nucleic acid that encodes a polypeptide of interest. The cell in which the recombinant polypeptide is produced can be used directly in the methods of the invention, or the recombinant polypeptide can be purified from the culture medium or from a lysate of the cells.

Variants of the aggregation-disposed polypeptides can also be used in the methods of the invention and can be prepared by substituting selected amino acids in these polypeptides. A variant of an aggregation-disposed polypeptide includes a polypeptide which has high sequence identity (e.g., 60%, 70%, 80%, 90, 95, 96, 97, 98 or 99%) to an aggregation-disposed polypeptide of above and retains the ability to aggregate.

Also useful for the methods of the invention are aggregation-competent portions of the naturally occurring aggregation-disposed polypeptides, e.g., a fragment of a naturally occurring polypeptide containing an extended polyglutamine region or other region that promotes aggregation of the parent protein with copies of itself or with a different protein.

Also included in the invention are aggregation-disposed fusion proteins, e.g., a fusion protein containing an extended polyglutamine region and a green fluorescent protein (GFP) (which term includes enhanced GFP, or "EGFP").

Nucleic Acid Molecules

Isolated nucleic acid molecules that encode naturally occurring, aggregation-disposed polypeptides, variants thereof, or non-naturally occurring aggregation-disposed polypeptides are useful in the methods of the invention. Naturally occurring nucleic acid sequences which encode aggregation-disposed polypeptides are well known in the art, e.g., sequences which encode huntingtin (Genbank accession #NM00211), atrophin-1 (Genbank accession #AF038564), ataxin-1 (Genbank accession #AL00931), ataxin-2 (Genbank accession #AF034373), ataxin-3 (Genbank accession #NM004993), alpha 1a-voltage dependent calcium channel (Genbank accession #AI660731), ataxin-7 (Genbank accession #AI660731), androgen receptor (Genbank accession #AI759506), alpha, beta and gamma synucleins (Genbank accession ##NM003085, AI879167, and NM003087, respectively), amyloid light chain (Genbank accession #AF026929) and amyloid-associated protein (Genbank accession #AF053356). Nucleic acid sequences that encode fragments of naturally occurring, aggregation-disposed polypeptides which retain the ability to aggregate are also useful in the methods of the invention.

In some instances, it may be preferable to generate a non-naturally occurring polypeptide which encompasses a region (e.g., an extended stretch of contiguous glutamine residues) which is known to be involved in polypeptide aggregation. For example, in bacteria the ability to recombinantly produce a polypeptide with an extended polyglutamine region is difficult, possibly because DNA or RNA containing multiple contiguous CAG codons may form secondary structures which affect replication and/or transcription. Whatever the mechanism causing this difficulty, one can overcome it by using a nucleic acid sequence with alternating CAG and CAA codons to encode the polyglutamine region, e.g., alternating CAG and CAA codons or another pattern such as (CAA CAG CAG CAA CAG CAA)n (SEQ ID NO:1), where n can be between 5–300, e.g., n is 5, 6, 7, 8, 9, 10, 11, 12, 13, 14, 15, 16, 17, 18, 19, 20, 21, 22, 23, 24, 25, 26, 27, 28, 29, 30. The CAG and CAA codons need not be present in equal numbers and need not form a repeating pattern.

Expression Control Sequences and Vectors

Two ways in which the methods of the invention can be carried out are: (i) using a cell which has been genetically modified to express aggregation-disposed polypeptides; and (ii) using purified aggregation-disposed polypeptides.

Typically, expressing an aggregation-disposed polypeptide in a cell involves inserting an aggregation-disposed polypeptide coding sequence into a vector, where it is operably linked to one or more expression control sequences. The need for and identity of expression control sequences will vary according to the type of cell in which the aggregation-disposed polypeptide sequence is to be expressed. Examples of expression control sequences include transcriptional promoters, enhancers, suitable mRNA ribosomal binding sites, and sequences that terminate transcription and translation.

Suitable expression control sequences can be selected by one of ordinary skill in the art. Standard methods can be used by the skilled person to construct expression vectors. See, generally, Sambrook et al., 1989, *Cloning—A Laboratory Manual* (2nd Edition), Cold Spring Harbor Press.

Vectors useful in this invention include plasmid vectors and viral vectors. Viral vectors can be, for example, those derived from retroviruses, adenovirus, adeno-associated virus, SV40 virus, pox viruses, or herpes viruses. Once introduced into a host cell (e.g., bacterial cell, yeast cell, insect cell, avian cell, or mammalian cell), the vector can remain episomal, or be incorporated into the genome of the host cell. Useful vectors include vectors which can be purchased commercially, e.g., pcDNA 3.1-based vectors can be purchased from Invitrogen, Carlsbad, Calif. pcDNA 3.1-based vectors include the human cytomegalovirus (CMV) immediate-early promoter/enhancer for high level expression in mammalian cell lines, and bovine growth hormone (BGH) polyadenylation signal for efficient transcript stabilization and termination.

To generate a purified preparation of the aggregation-disposed polypeptide for use in the present method, the aggregation-disposed polypeptide can be produced recombinantly in a cell (as described above) and then purified from that cell, or the polypeptide can be made synthetically. Since aggregation-disposed polypeptides aggregate, it may be necessary to take certain steps when producing and isolating the polypeptide so that a soluble, non-aggregated form of the polypeptide can be obtained. For example, it is preferable when producing the polypeptide recombinantly in a cell not to over-produce the polypeptide, as over-production of aggregation-disposed polypeptides in a cell may result in polypeptide aggregation.

Labeling Polypeptides

The aggregation-disposed polypeptides can be chemically coupled to a label or recombinantly expressed as a fusion protein with a label. Examples of labels include various enzymes, fluorescent materials, luminescent materials, and bioluminescent materials. Examples of suitable enzymes include horseradish peroxidase, alkaline phosphatase, β-galactosidase, and acetylcholinesterase; examples of suitable fluorescent materials include umbelliferone, fluorescein, fluorescein isothiocyanate, rhodamine, dichlorotriazinylamine fluorescein, dansyl chloride and phycoerythrin; an example of a luminescent material is luminol; and examples of bioluminescent materials include luciferase, luciferin, and aequorin.

The coupling of a label to a polypeptide of the invention can be carried out by chemical methods known in the art. A variety of coupling agents, including crosslinking agents, can be used for covalent conjugation. Examples of crosslinking agents include N,N'-dicyclohexylcarbodiimide (DCC; Pierce), N-succinimidyl-S-acetyl-thioacetate (SATA), N-succinimidyl-3-(2-pyridyldithio)propionate (SPDP), ortho-phenylenedimaleimide (o-PDM), and sulfo-succinimidyl 4-(N-maleimidomethyl) cyclohexane-1-carboxylate (sulfo-SMCC). See, e.g., Karpovsky et al., *J. Exp. Med.* 160:1686, 1984; and Liu et al., *Proc. Natl. Acad. Sci. USA* 82:8648, 1985. Other methods include those described by Paulus, *Behring Ins. Mitt.*, No. 78, 118–132, 1985; Brennan et al. *Science* 229:81–83, 1985, and Glennie et al., *J. Immunol.* 139:2367–2375, 1987. A large number of coupling agents for polypeptides, along with buffers, solvents, and methods of use, are described in the Pierce Chemical Co. catalog, pages T-155–T-200, 1994 (3747 N. Meridian Rd., Rockford Ill. 61105, U.S.A.,; Pierce Europe B. V., P.O. Box 1512, 3260 BA Oud Beijerland, The Netherlands), which catalog is hereby incorporated by reference.

Fluorescence labeling can be achieved by purifying an aggregation-disposed polypeptide and covalently conjugating the polypeptide to a reactive derivative of an organic fluorophore. Examples of suitable fluorophores include fluorescein, rhodamine, Texas Red, and the like. Fluorescence may be detected by any method known in the art, e.g., using fluorescent microscopy, a fluorometer, or fluorescence-activated cell sorting (FACS).

Where the label is a protein, e.g., an enzyme or a fluorescent protein, it can be made an integral part of the aggregation-disposed polypeptide by expressing the two together as a recombinant fusion protein, as discussed above. Suitable fluorescent proteins include green fluorescent protein (GFP) and blue fluorescent protein (BFP).

The GPF gene was originally cloned from the jellyfish Aequorea Victoria. It encodes a protein of 238 amino acids which absorbs blue light (major peak at 395 nm) and emits green light (major peak at 509 nm) (Prasher et al., *Gene* 15:229–223, 1992). GPF genes and functional proteins have been identified in a variety of organisms in the phyla hydrozoa, cnidaria, anthozoa and ctenophora.

Both wild-type GFP and mutated GFP from *Aequorea Victoria* can be used as a label. The mutation of GFP (e.g., the substitution of certain amino acids in the GFP polypeptide) has been reported to yield GFP proteins with improved spectral properties. For example, mutating serine 65 to a threonine generates a GFP variant which has about sixfold greater brightness than wild-type GFP (Heim et al., *Nature* 372:663–664, 1995). The coding sequence for an enhanced GFP can be purchased commercially (Clontech, Palo Alto, Calif.).

BPF can also be used as a label. To obtain BFP, tyrosine 66 of GFP is mutated to a histidine. This mutated GFP protein fluoresces bright blue, in contrast to the green of the wild-type protein.

Screening Assays

The invention encompasses methods for identifying compounds that disrupt the aggregation of particular polypeptides, e.g., the aggregation of huntingtin polypeptides. Candidate compounds that can be screened in accordance with the invention include polypeptides, peptide mimetics, antibodies, and monomeric organic compounds, i.e., "small molecules." In particular, certain classes of compounds may be chosen by one skilled in the art based on knowledge of the mechanism of aggregation of particular aggregation-disposed polypeptides. For example, aggregation of huntingtin polypeptides is believed to be mediated by hydrogen bond formation. Based on this, compounds such as D-amino acid-containing peptides and compounds that compete for H bond formation can be tested by the method of the invention to determine if these compounds function as useful aggregation disrupting compounds.

Labels

To determine if a compound disrupts polypeptide aggregation, a method of detecting the extent to which polypeptides aggregate in the presence of the compound is required. This is accomplished in the methods of the invention by labeling the aggregation-disposed polypeptide with a detection moiety, a detectable property of which changes (i.e., is lost, gained, or changed in character) directly or indirectly, based on whether the polypeptide is in an aggregated state or not. For example, in one embodiment, the property of the detection moiety is eliminated, or at least decreased, as a consequence of aggregation, so that the label on the unaggregated polypeptide exhibits the property while the label on the aggregated polypeptide does not. An example of this would be an enzymatic label which is active only when in an unaggregated state. Alternatively, the inverse can be true. For example, when a denaturant-sensitive label is used, exposure to a denaturant abolishes the detectable property of the label, if the label is linked to a non-aggregated polypeptide. Once the polypeptides aggregate, the detection moiety is protected from the denaturant and retains its detectable property even after treatment with the denaturant. The label can be any denaturant-sensitive detection moiety, e.g., enzymatic or fluorescent.

Where the label is an enzyme, a property of the enzyme, e.g., the ability to catalyze a particular reaction, may alter as a consequence of aggregation. For example, upon aggregation, the enzymatic activity of the label may be eliminated. Thus, the extent of polypeptide aggregation in the presence of the test compound is determined by determining the ability of the enzyme to catalyze the reaction. An increase in the amount of enzyme activity in the presence of the test compound, as compared to a control, indicates that the compound is an aggregation disrupting compound.

Alternatively, the enzyme may be one which is inactivated in the presence of a denaturant. Since aggregation protects the enzyme from denaturing, addition of a denaturant permits one to determine whether the polypeptide linked to the enzyme is aggregated or not. If the amount of enzyme activity is lower in the presence of denaturant and test compound, compared to denaturant alone, the test compound is a putative aggregation disrupting compound.

Where the label is a fluorescent protein, e.g., a GFP, the ability of the fluorescent-labeled polypeptide to fluorescence in the presence of a denaturant following aggregation is determined. For example, when GFP is used as the label, the addition of a denaturant causes the soluble, non-aggregated, GFP-labeled polypeptides to denature, thereby quenching fluorescence. In contrast, aggregated GFP-labeled proteins are sufficiently protected from the denaturant so that the GFP of the aggregated GFP-labeled polypeptides will continue to fluoresce in the presence of the denaturant. Thus, a decrease in fluorescence of the GFP-labeled polypeptide in the presence of denaturant plus test compound, as compared to a control with denaturant alone, indicates that the test compound is an aggregation disrupting compound.

The label can also be a selectable marker, such as an antibiotic resistance marker. In this instance, the aggregation-disposed polypeptide is expressed in a cell as a fusion with a selectable marker, e.g., neomycin phosphotransferase (neo). The aggregation of polypeptides fused to selectable markers in a cell inhibits the ability of the selectable marker to confer antibiotic resistance on that cell during selection. Thus, where a selectable marker is used, the ability of the polypeptides to aggregate in the presence of a compound is determined by measuring cell viability in the presence of a selection agent, e.g., an antibiotic. For example, where the selection marker is neo, the selection agent aminoglycoside G-418 can be used, or where the selectable marker is hygro, the selection agent is typically hygromycin. An increase in cell viability in the presence of a test compound plus selection agent, compared to the selection agent alone, is an indication that the test compound is an aggregation disrupting polypeptide.

Identification of a Compound that Disrupts the Aggregation of Aggregation-disposed Polypeptides In one screening method of the invention, labeled (e.g., GFP labeled) aggregation-disposed polypeptides are incubated with a test compound of interest. Following a period of time sufficient to permit polypeptide aggregation, the polypeptide/test compound mixture is contacted with a denaturant. The denaturant can be any agent (e.g., heat, urea, guanidine HCL, a detergent such as Triton or sodium dodecyl sulfate, or a mixture thereof) that is able to quench fluorescence of non-aggregated GFP-labeled polypeptides, but which is unable significantly to quench fluorescence of aggregated GFP-labeled polypeptides. The extent of aggregation in the presence of the test compound is determined by measuring fluorescence. Fluorescence can be measured by any method known in the art, e.g., using a fluorometer. A decrease in the amount of denaturant-resistant fluorescence in the presence of the test compound, as compared to a control, is an indication that the test compound is an aggregation disrupting compound.

The above method requires that at least two aggregation-disposed polypeptides are contacted. In this method, both polypeptides can be in solution (e.g., in a cell or in vitro), or alternatively one of the aggregation-disposed polypeptides can be immobilized, e.g., a GST-GFP-labeled aggregation-disposed polypeptide can be immobilized on a polymeric bead or a plastic dish, coated with glutathione.

A variation of the above method involves expressing aggregation-disposed polypeptides in a cell in the presence of a test compound of interest. The cell is transfected with an expression vector containing a nucleotide sequence that encodes a labeled aggregation-disposed polypeptide, and contacted with the test compound. Following a suitable incubation period that permits expression and aggregation of polypeptides within the cell, the cell is contacted with a denaturant, e.g., a detergent, and the function of the label is measured. Where the label is a GFP or BFP, the amount of fluorescence in the cell is measured and compared to a control cell that was not exposed to the test compound. A decrease in fluorescence in a cell exposed to the test compound, as compared to a control cell, is an indication that the test compound disrupts polypeptide aggregation.

The above method can be performed in any cell, such as an immortalized cell, a primary cell, or a secondary cell. Examples of immortalized cells include COS, Chinese hamster ovary (CHO), HeLa, Vero, WI38, HepG2, 3T3, RIN, MDCK, A549, PC12, K562 and 293 cells. Neuronal cells can be used, as well.

Typically, the aggregation-disposed polypeptides are expressed in a cell using an expression vector. A person skilled in the art would be able to choose an appropriate expression vector. For example, expression vectors for use in mammalian cells ordinarily include an origin of replication and a promoter located in front of the gene to be expressed. A polyadenylation site and transcriptional terminator sequence are preferably included. Ribosome binding sites and RNA splice sites may also be included. An example is the SV40 late gene 16S/19S splice/donor acceptor signal. The promoter in the expression vector can be a constitutive promoter or an inducible promoter. Preferably, expression of the aggregation-disposed polypeptide is under the control of an inducible promoter. Commercially available inducible expression systems can be used, e.g., the ecdysone-inducible expression system (Invitrogen, Carlsbad, Calif.; see example section).

A vector which expresses the aggregation-disposed polypeptides may be introduced into cells by a variety of physical or chemical methods, including electroporation, microinjection, microprojectile bombardment, calcium phosphate precipitation, and liposome-, polybrene-, or DEAE dextran-mediated transfection. Alternatively, infectious vectors such as retroviral, herpes, and adenovirus-associated vectors can be used to introduce the DNA.

Administration of the Polypeptide Aggregation Disrupting Compound

Once a given compound is found to have aggregation-disrupting activity in one of the above screening methods, it can be tested for safety and efficacy in an animal model (if there is one) for the disease(s) associated with the aggregation-disposed polypeptide, or in a human susceptible to the disease.

Administration of the compound to a subject (e.g., a human) may be by any known technique. The compound can be administered to a subject by oral ingestion, intravenous injection, intramuscular injection, intrathecal injection, or bronchi-nasal spraying. The invention also pertains to a pharmaceutical composition of the aggregation disrupting compound. The composition includes the compound in a therapeutically effective amount sufficient to inhibit (i.e., decrease) the aggregation of the target polypeptides in cells of the patient, and a pharmaceutically acceptable carrier. A "therapeutically effective amount" refers to an amount effective, at dosages and for periods of time necessary, to achieve the desired result. A therapeutically effective amount of the compound may vary according to factors such as the disease state, age, sex, and weight of the individual. Dosage regimens may be adjusted to provide the optimum therapeutic response. A therapeutically effective amount is also one in which any toxic or detrimental effects of the compound is outweighed by the therapeutically beneficial effects.

One factor that may be considered when determining a therapeutically effective amount of a compound is the concentration of the target polypeptide in a biological compartment of a subject, such as in the cerebrospinal fluid (CSF) or brain of the subject. For example, the concentration of natural beta-amyloid protein in the CSF has been estimated at 3 nM (Schwartzman, *Proc. Natl. Acad. Sci. USA* 91:8368–8372, 1994). A non-limiting range for a therapeutically effective amount of a beta amyloid aggregation disrupting compound in the CNS is 0.01 nM–10 $\mu$M. It is to be noted that dosage values may vary with the severity of the condition to be alleviated.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral administration. More preferably, the carrier is suitable for administration into the central nervous system (e.g., intraspinally or intracerebrally). Pharmaceutically acceptable carriers include sterile powders, aqueous solutions and dispersions, for example, water, ethanol, polyol (for example, glycerol, propylene glycol, liquid polyethylene glycol, and the like), and suitable mixtures thereof.

EXAMPLES

Example 1

Generating Polypeptides with Extended Polyglutamine Regions

In order to circumvent difficulties associated with the propagation of long CAG repeats in bacteria, a cloning strategy was developed which used a mixture of CAG/CAA codons which encode 25 glutamine residues (normal in Huntington disease (HD)), 104 glutamine residues (known to be pathological in HD), and 191, 230, and 300 glutamine residues (all of which are longer than the longest polyglutamine regions observed in HD).

In order to synthesize a sequence which has a mixture of CAG/CAA codons, CAA CAG CAG CAA CAG CAA (SEQ ID NO:1) and complementary TTG TTG CTG TTG CTG CTG (SEQ ID NO:2) oligonucleotides were annealed to generate double stranded duplex DNA with trinucleotide extensions. These short duplex DNA molecules were used as starting material for two consecutive ligations to obtain sequences that contain a mixture of CAG/CAA codons (CAA CAG CAG CAA CAG CAA)$_n$ (SEQ ID NO:1) of different lengths. The ligation reaction was terminated by addition of dsDNA linkers that included 5' trinucleotide extensions and the restriction sites HindIII at 5' and PstI at 3' with respect to the CAG/CAA DNA strand. Sequences containing the mixture of CAG/CAA codons were subcloned into Bluescript-KS vector and maintained in XL-1 Blue (Stratagene, La Jolla, Calif.). The CAA CAG CAG CAA CAG CAA (SEQ ID NO:1) consensus was verified by two-strand sequence analyses. Proteins encoded by the DNA were found to be stable in bacteria.

To generate mammalian expression constructs, a short huntingtin N-terminus cDNA fragment, including Kozak box, start codon and first sixteen amino acids, was amplified by PCR (Amplitaq, Perkin Elmer), ligated with various polyglutamine repeats (25Q, 104Q, 191Q, 230Q, 250Q, and 300Q), and subcloned into pcDNA 3.1 (Invitrogen, Carlsbad, Calif.).

To monitor the formation of aggregates in cells, polyglutamines were fused at the carboxy (C)-terminus with either a 28 amino acid c-myc tag, or with a 230 amino acid enhanced green fluorescent protein tag (EGFP; Clontech, Palo Alto, Calif.). The first methionine of the EGFP sequence was replaced by lysine in the polyglutamine (polyQ)/EGFP constructs.

Example 2

Extended PolyQ Polypeptides Form Cytoplasmic and Perinuclear Aggregates

The ability of synthetic polypeptides containing extended polyQ regions to form aggregates was tested in cells such as COS-1, COS-7, NIH 3T3, 293, EcR-293, eHela, NT-2, and PC-12. Cells were grown on cover slips to 50% confluence and lipofected for two hours with Transfectam reagent (Promega, Madison, Wis.) and plasmids encoding the c-myc-tagged or EGFP-tagged polyglutamines of various lengths. Polyglutamine aggregation was assayed from 16 to 72 hours after transfection. Cells were fixed in 2% formaldehyde/0.1% Triton-X100 for 10 minutes and incubated with primary mouse monoclonal anti-c-myc (Invitrogen, Carlsbad, Calif.) antibody (1:500) and secondary FluoroLink Cy3™ (Amersham Life Science) antibody (1:2000). Nuclei were stained with 4'-6-diamidino-2-phenylindole (DAPI). Epifluorescent microscopy was performed on a Zeiss Axioplan II™ equipped with a Quantix CCD™ camera (Photometrics, Tuscan, Ariz.) and IPLab Spectrum™ imaging software (Scanalytics, Fairfax, Va.).

Normal length (25Q) synthetic polyglutamines always showed diffuse cytoplasmic expression by fluorescence microscopy. In contrast, extended polyglutamines (104Q, 191Q, 230Q, 300Q) were found to aggregate in the mammalian cell lines tested. Early in the time course of precipitation, extended polyQ formed small, star-like aggregates, which were detected in COS-1 cells as early as 16 hours after transfection. Within 36 hours after transfection, polyQ aggregates grew into dense, brilliantly fluorescent spherical structures, which could be as large as 4 to 5 microns. Polyglutamine aggregates were found to be located exclusively in the cytoplasm, often in the perinuclear space or associated with the nuclear membrane. While no significant difference in number or size of aggregates using either the c-myc or the EGFP-tagged extended polyQ constructs was observed, the polyQ/c-myc aggregates which were detected by means of fluorescent antibody stained the aggregate with an intense peripheral rim. Thus, polyQ aggregates form a very dense structure which is impenetrable to the antibody. In contrast, the fluorescence of the intrinsically fluorescent polyQ/EGFP aggregates typically came from inside the core of the aggregate. Since denatured EGFP lacks fluorescence, this observation suggested that polypeptides inside the aggregate were at least partially in native form.

Example 3

Nuclear Localization of Aggregates Depends on Flanking Sequence of Extended PolyQ Polyglutamine aggregates have been found in HD brain in dystrophic neurites in the cortex and white matter and as nuclear inclusions in the striatum. Using the cell culture described herein, extended polyQ aggregates were found in the cytoplasm of transfected cells, as opposed to the nucleus. Since the constructs have only a small N-terminal fragment of huntingtin, this may mean that the C-terminus of huntingtin includes a nuclear localization signal (NLS). Such a putative NLS would cause slow accumulation of mutant huntingtin in the nucleus and eventual formation of nuclear inclusions. To test the effect of a strong NLS on the subcellular localization of aggregates, the nucleolin protein (650 amino acids), which has strong nuclear and nucleolus localization signals, was chosen.

Expression constructs (polyQ/nucleolin/EGFP) were generated by inserting nucleolin cDNA between polyQ-encoding and EGFP-encoding sequences as follows. A nucleolin cDNA sequence was amplified by PCR and inserted between polyglutamine (25Q, 104Q, 300Q)-encoding and EGFP-encoding sequences in HD polyQ EGFP constructs. The first methionine codon of nucleolin cDNA was changed to a lysine codon in these polyQ/nucleolin/EGFP constructs.

When normal length poly25Q/nucleolin/EGFP and extended polyQ/nucleolin/EGFP fusion proteins were expressed in cells, it was found that all polypeptides were located in the nucleus, and particularly in the nucleoli. Moreover, the length of the fusion protein, which ranged up to 1200 amino acids, did not limit nuclear translocation and aggregation. No fluorescent signal was seen in the cytoplasm.

In another approach, the naturally occurring stretch of 38 polyglutamines in the TATA-binding protein (TBP) was extended to 104Q so as to target aggregate formation to the nucleus and directly study the effects of polyQ aggregation in the nucleus. Wild-type TBP cDNA was amplified from genomic DNA extracted from Ehela. To replace the native 38Q homopolymeric stretch in the TBP sequence, sequences encoding N-terminal and C-terminal fragments of TBP (Genbank accession #M55654) were amplified by PCR with primers introducing novel internal HindIII and PstI restriction sites at nucleotide positions 412 and 521, respectively. DNA fragments encoding 25Q, 42Q, 65Q and 104Q were ligated with the sequences encoding N-terminal and C-terminal TBP fragments, and subcloned into pcDNA 3.1. Finally, the TBP proteins were tagged with c-myc at the C-terminus.

As predicted, TBP/42Q, TBP/65Q and TBP/104Q formed multiple aggregates, which were clearly located within the nucleoplasm. The subcellular localization of polyQ aggregates was determined by polyQ flanking sequences. Additionally, it was found that a sequence of at least 1000 amino acids can be translocated into the nucleus by active transport and aggregated without cleavage.

In previous experiments, polyQ aggregates were found exclusively in the cytoplasm, unless the extended polyQ construct included nucleolin. To determine whether the strong nuclear localization signal could also function in trans, a construct encoding an extended poly104Q/nucleolin/EGFP fusion protein was coexpressed with a construct encoding extended polyQ/c-myc, which lacks an NLS. In this experiment, the polyQ/c-myc fusion protein was detected in heterogeneous aggregates in the nucleus. Nuclear localization was strictly dependent on co-aggregation with poly104Q/nucleolin/EGFP fusion protein. Despite the presence of the strong nuclear localization signal in cis, it was found that polyQ/nucleolin/EGFP also aggregated with polyQ/c-myc in the cytoplasm of some cells, and was excluded from the nucleus. Thus, subcellular localization of aggregation depends in general upon the functional characteristics of the protein in which the polyQ is embedded. Nonetheless, strong intermolecular interactions mediated by polyQ domains can in some cases be sufficient to override the effects of such intrinsic localization signals.

Example 4

Certain Polylglutamine-containing Cellular Proteins Can Co-aggregate with Extended PolyQ To establish whether a normal length polyglutamine polypeptide of 25 glutamine residues can interact with and perhaps aggregate with extended polyglutamines, the polypeptides were co-expressed in cells as follows. Normal length poly25Q/EGFP and extended poly104Q/c-myc were expressed alone or co-expressed. Normal length polyQ polypeptides showed a diffuse pattern of expression when expressed alone. Remarkably, these same normal length polyglutamines were recruited into cellular aggregates when they were coexpressed with extended polyglutamines. In contrast, when EGFP lacking a polyQ segment was co-expressed with extended polyQ/c-myc, EGFP fluorescence was not detected in aggregates. Co-expression experiments using poly25Q/nucleolin/EGFP and extended polyQ/c-myc yielded flourescent co-aggregates in nucleoli, whereas EGFP/nucleolin co-expressed with extended polyQ/c-myc gave cytoplasmic aggregates which had no EGFP signal. These results demonstrate the strict polyglutamine-dependent nature of the co-aggregation phenomenon. The results further suggest that intermolecular interactions that occur between mutant extended polyQ and normal cellular proteins with significant glutamine stretches (below a threshold of 31) may play a role in the cellular pathology of the polyglutamine neurodegenerative disorders. To investigate this possibility in the cell culture system, the nuclear transcriptional co-activator CREB-binding protein (CBP), which, like several such proteins, has a glutamine-rich C-terminus within which is a homopolymeric stretch of 19 glutamine residues, was tested.

To express full length CBP, CPB cDNA (GenBank accession #U47741) was cloned into the expression vector pcDNA 3.1. The sequence encoding the polyglutamine-rich domain near the C-terminus of CPB was removed by digesting with SacII and XbaI, amplifying the 3'-end fragment with primers containing SacII and XbaI sites, then fusing with the 5'-end fragment. This results in approximately a 200 amino acid deletion (6652–7228 nt) at the C-terminus which removes a polyglutamine-rich fragment, including a 19Q homopolymeric stretch. Both full length and deletion proteins were tagged with c-myc at the C-terminus.

Co-expression of the 25Q/EGFP construct with the construct encoding c-myc-tagged, full-length CBP showed a diffuse cytoplasmic localization. In contrast, when c-myc-tagged, full-length CBP was coexpressed along with extended polyQ constructs, CBP was detected within cytoplasmic aggregates. As predicted, CBP which was co-expressed with 104QTBP forms aggregates in the nucleus. In sharp contrast, however, when CBP was co-expressed with 104Q/nucleolin, no CBP was detected in the nucleolar aggregates. This failure to detect CBP in the nucleolar aggregates can be explained by the subcellular and subnuclear location of CBP itself. While transfected CBP is seen strongly in the nucleus and weakly in the cytoplasm, it is clearly excluded from nucleolar bodies. These results suggest that the likelihood that an endogenous cellular polyQ containing protein will be found in a polyQ aggregate may depend on the interplay between a number of factors including local concentration within the cell. In particular, the ability of mutant extended polyQ to recruit cellular proteins into aggregates may be exquisitely dependent on co-localization within precise subcellular compartments. To determine whether co-aggregation of CBP and 104Q/EGFP is mediated by the homopolymeric polyQ domain, a CBP construct which encodes a c-myc-tagged CBP lacking the glutamine-rich region was co-transfected with a construct encoding 104Q/EGFP. No c-myc signal was detected in the aggregates in the majority of co-transfected cells. Thus, it was clearly demonstrated that recruitment of cellular proteins into polyQ aggregates is dependent upon interactions between polyQ domains.

Example 5

Insoluble PolyQ Aggregates Shield Entrapped Polypeptides and Protect Them from Denaturation, Even Under Harsh Conditions In order to investigate further the nature of the very insoluble aggregates, a novel in situ assay to test the resistance of cellular aggregates to high concentrations of detergents was developed. Cells were transfected with a construct encoding either normal length poly25Q/EGFP, or extended poly104Q/EGFP. Forty hours later, cells were treated in situ with SDS/Triton X-100, at various concentrations as high as 5% SDS/5% Triton X-100, overnight at room temperature. High intensity EGFP fluorescence was detected in surviving aggregates formed by extended poly104Q/EGFP polypeptides after treatment with detergents. In contrast, soluble, non-aggregated EGFP and poly25Q/EGFP were completely denatured by detergents, and EGFP fluorescence was no longer detected. The results show that high concentrations of detergents are unable to destroy polyQ aggregates or to denature the native EGFP structure once it is bound in an aggregate.

Example 6

Extended PolyQ Peptides Trap Soluble, Normal Length PolyQ Peptides into Insoluble, Detergent-resistant Aggregates in Cells To demonstrate directly that extended polyQ peptides are able to trap normal length polyQ peptides into insoluble aggregates in the cell, and are not simply loosely associated or co-localized, co-aggregates were treated with high concentrations of detergents as described above. Cells were co-transfected with constructs encoding poly25Q/EGFP and extended polyQ104/c-myc, producing co-aggregates. These co-aggregates were extracted from the cells and were shown to be resistant to high concentrations of detergents. The fluorescence due to protection by the co-aggregation of native normal length poly25Q/EGFP with extended polyQ was identical to the fluorescence in aggregates formed by extended poly104Q/EGFP alone. In control experiments, cells were co-transfected with constructs encoding EGFP (lacking a polyQ segment) and extended polyQ/c-myc. Treatment with detergent denatured both soluble poly25Q/EGFP and EGFP lacking a polyQ segment, such that EGFP fluorescence was no longer detected. Thus, detergent-resistant insolubility was shown to be dependent upon interactions between the polyQ stretches themselves.

Example 7

System for High Throughput Screening for Agents to Suppress Polyglutamine Aggregation The above results indicate that aggregated polyglutamines can form strong interactions. Molecules that might interact with extended polyglutamines and thereby suppress aggregation would be of potential therapeutic benefit. Identification of such molecules in a cell culture system would require the reliable induction of extended polyglutamine aggregates. As a first step toward this goal, ecdysone-inducible mammalian cell lines that expressed EGFP-tagged 25Q, 104Q and 300Q in a ligand-dependent manner were generated as follows.

EGFP and polyQ/EGFP fusions with 25Q, 104Q and 300Q were subcloned into pIND DNA vector (Invitrogen, Carlsbad, Calif). EcR-2 93 cells (Invitrogen, Carlsbad, Calif.) were transfected with pIND DNA using Transfectam IM reagent (Promega, Madison, Wis.). Stable integrants were selected in 0.4 mg/ml G418 and 0.4 mg/ml Zeocin. PolyQ expression and aggregation were tested in isolated cell lines by induction with 0–20 $\mu$M Muristerone A and Ponasterone A. Cells from selected clones showed uniform fluorescence after induction. The expression of polypeptides containing an extended polyglutamine region and the number of aggregates formed were dose-dependent. Aggregates were detected as early as 24 hr after induction, with maximum appearance at 48–72 hr. Typically, 2–3 aggregates per colony of 12–16 cells were observed 48 hours after induction with 10 $\mu$M Muristerone A.

Transfected cells, induced with Muristerone, were harvested from Petri dishes, washed twice with PBS, lysed with 0.3% NP-40, and washed with 0.1% Triton X-100/PBS. Simultaneously, floating aggregates from dead cells were pelleted from culture media by high-speed centrifugation, washed with PBS and 0.1% Triton X-100/PBS and combined with cell lysates. Aggregates were washed twice with 1% Triton X-100/PBS for 1 hour (or overnight) and washed in 0.1% SDS. Aggregates were pelleted after each wash by centrifugation. Finally, semi-purified aggregates were incubated with 2–5% SDS/2–5% Triton X-100 mix for 1–48 hours at room temperature (37° C.). Alternatively, live cells expressing polyQ/EGFP fusions were lysed in situ with 2–5% SDS/2–5% Triton-X-100.

When treated in situ with 5% SDS/5% Triton X-100, EGFP fluorescence was protected in polyQ aggregates even after 48 hours of detergent treatment at 37° C. In contrast, soluble, non-aggregated, EGFP-tagged material was denatured instantly and completely, and fluorescence no longer detected. This fluorescence quenching means to assess solubility is simple to generate, highly reproducible, and straightforward to score, due to the very intense fluorescent signal generated by the aggregated polyglutamines compared to the total absence of fluorescence seen with soluble molecules treated with denaturant.

What is claimed is:

1. A method of identifying a compound that disrupts the aggregation of polypeptides containing extended polyglutamine regions, the method comprising:

provifing a fluorescently labeled first polypeptide, wherein the first polypeptide contains an extended polyglutamine region and the fluorescent label is a polypeptide;

contacting the first polypeptide with (a) a second polypeptide, wherein the second polypeptide contains an extended polyglutamine region, and (b) a test compound, wherein the first polypeptide, the second polypeptide, and the test compound form a mixture;

contacting the mixture with a denaturant; and detecting fluorescence, wherein a decrease in fluorescence in the presence of the test compound, relative to control, indicates that the fluorescently labeled first polypeptide did not aggregate with the second polypeptide and that the test compound is, therefore, a compound that disrupts polypeptide aggregation.

2. The method of claim 1, wherein the first or second polypeptide is a polypeptide comprising at least 32 consecutive glutamine residues.

3. The method of claim 1, wherein the first polypeptide or the second polypeptide is huntingtin.

4. The method of claim 1, wherein the first or second polypeptide is immobilized.

5. The method of claim 1, wherein the first and second polypeptides are in solution.

6. The method of claim 1, wherein the first polypeptide or the second polypeptide is atropin-1.

7. The method of claim 1, wherein the first polypeptide or the second polypeptide is ataxin-1.

8. The method of claim 1, wherein the first polypeptide or the second polypeptide is ataxin-2.

9. The method of claim 1, wherein the first polypeptide or the second polypeptide is ataxin-3.

10. The method of claim 1, wherein the first polypeptide or the second polypeptide is ataxin-7.

11. The method of claim 1, wherein the first polypeptide or the second polypeptide is alpha 1A.

12. The method of claim 1, wherein the first polypeptide or the second polypeptide is an androgen receptor.

13. The method of claim 1, wherein the first polypeptide or the second polypeptide is a tau protein.

14. The method of claim 1, wherein the first polypeptide and the second polypeptide are identical to one another.

15. The method of claim 1, wherein the first polypeptide and the second polypeptide are different from one another.

16. The method of claim 1, wherein the fluorescently labeled first polypeptide is labeled with a green fluorescent protein.

17. The method of claim 1, wherein the fluorescently labeled first polypeptide is labeled with a blue fluorescent protein.

18. The method of claim 1, wherein the denaturant is a detergent.

19. A method of identifying a compound that disrupts polypeptide aggregation, the method comprising:

providing a fluorescently labeled first polypeptide, wherein the fluorescent label is a polypeptide;

contacting the fluorescently labeled first polypeptide with a second polypeptide and a test compound to form a mixture;

contacting the mixture with a denaturant; and detecting fluorescence, wherein a decrease in fluorescence in the presence of the test compound, relative to control, indicates that the fluorescently labeled first polypeptide did not aggregate with the second polypeptide and that the test compound is, therefore, a compound that disrupts polypeptide aggregation.

20. The method of claim 19, wherein the first or second polypeptide is a polypeptide comprising at least 32 consecutive glutamine residues.

21. The method of claim 19, wherein the first polypeptide or the second polypeptide is huntingtin.

22. The method of claim 19, wherein the first polypeptide or the second polypeptide is atropin-1.

23. The method of claim 19, wherein the first polypeptide or the second polypeptide is ataxin-1.

24. The method of claim 19, wherein the first polypeptide or the second polypeptide is ataxin-2.

25. The method of claim 19, wherein the first polypeptide or the second polypeptide is ataxin-3.

26. The method of claim 19, wherein the first polypeptide or the second polypeptide is ataxin-7.

27. The method of claim 19, wherein the first polypeptide or the second polypeptide is alpha 1A.

28. The method of claim 19, wherein the first polypeptide or the second polypeptide is an androgen receptor.

29. The method of claim 19, wherein the first polypeptide or the second polypeptide is a tau protein.

30. The method of claim 19, wherein the first polypeptide and the second polypeptide are identical to one another.

31. The method of claim 19, wherein the first polypeptide and the second polypeptide are different from one another.

32. The method of claim 19, wherein the fluorescently labeled first polypeptide is labeled with a green fluorescent protein.

33. The method of claim 19, wherein the fluorescently labeled first polypeptide is labeled with a blue fluorescent protein.

34. The method of claim 19, wherein at least one of the denaturant is a detergent.

\* \* \* \* \*

UNITED STATES PATENT AND TRADEMARK OFFICE
CERTIFICATE OF CORRECTION

| | | |
|---|---|---|
| PATENT NO. | : 6,420,122 B1 | Page 1 of 1 |
| APPLICATION NO. | : 09/405048 | |
| DATED | : July 16, 2002 | |
| INVENTOR(S) | : Housman et al. | |

It is certified that error appears in the above-identified patent and that said Letters Patent is hereby corrected as shown below:

Please insert the following In the specification of U.S. Patent No. 6,420,122 at column 1, line 4:

-- Sponsorship Information
This invention was made with government support under Grant Number P01-CA042063, awarded by the National Institutes of Health. The government has certain rights in the invention. --

Signed and Sealed this
Twelfth Day of June, 2012

David J. Kappos
*Director of the United States Patent and Trademark Office*